(12) United States Patent
Andler

(10) Patent No.: US 10,413,387 B2
(45) Date of Patent: Sep. 17, 2019

(54) THREADED DENTAL IMPLANT

(71) Applicant: John Andler, Rochester Hills, MI (US)

(72) Inventor: John Andler, Rochester Hills, MI (US)

( * ) Notice: Subject to any disclaimer, the term of this patent is extended or adjusted under 35 U.S.C. 154(b) by 0 days.

(21) Appl. No.: 14/600,153

(22) Filed: Jan. 20, 2015

(65) Prior Publication Data
US 2016/0206406 A1 Jul. 21, 2016

(51) Int. Cl.
*A61C 8/00* (2006.01)
(52) U.S. Cl.
CPC .......... *A61C 8/0022* (2013.01); *A61C 8/0024* (2013.01); *A61C 8/0025* (2013.01)
(58) Field of Classification Search
CPC ... A61C 8/0025; A61C 8/0074; A61C 8/0024; A61C 8/0022; F16B 25/00; F16B 25/0047
USPC ...................................... 433/172–176, 201.1
See application file for complete search history.

(56) References Cited

U.S. PATENT DOCUMENTS

| | | |
|---|---|---|
| 3,466,748 A | 9/1969 | Christensen |
| 4,406,623 A | 9/1983 | Grafelmann et al. |
| 4,468,200 A | 8/1984 | Münch |
| 4,746,294 A | 5/1988 | Colombo et al. |
| 4,863,383 A | 9/1989 | Grafelmann |
| 5,000,686 A | 3/1991 | Lazzara et al. |
| 5,088,926 A | 2/1992 | Lang |
| 5,338,197 A | 8/1994 | Kwan |
| 5,435,723 A | 7/1995 | O'Brien |
| 5,527,183 A | 6/1996 | O'Brien |
| 5,620,323 A | 4/1997 | Bressman |
| 5,642,996 A | 7/1997 | Mochida et al. |
| 5,964,768 A | 10/1999 | Huebner |
| 5,967,783 A | 10/1999 | Ura |
| 6,036,491 A * | 3/2000 | Hansson ............ A61B 17/8625 433/174 |
| 6,149,432 A | 11/2000 | Shaw et al. |
| 6,315,564 B1 | 11/2001 | Levisman |
| 6,468,277 B1 | 10/2002 | Justin et al. |
| 6,997,711 B2 | 2/2006 | Miller |
| 7,806,693 B2 | 10/2010 | Hurson |
| 8,066,511 B2 | 11/2011 | Wöhrle et al. |
| 2005/0095550 A1 | 5/2005 | Kim et al. |
| 2006/0204930 A1 | 9/2006 | Sul |

(Continued)

FOREIGN PATENT DOCUMENTS

| | | |
|---|---|---|
| DE | 10 2008 063 397 A1 | 7/2010 |
| DE | 10 2009 050 049 A1 | 4/2011 |
| DE | 10 2011 101 253 A1 | 8/2012 |

OTHER PUBLICATIONS

Semblex Delta PT Screw PDF (Sep. 16, 2008).*

(Continued)

*Primary Examiner* — Nicholas D Lucchesi
(74) *Attorney, Agent, or Firm* — Kutak Rock LLP

(57) ABSTRACT

A threaded dental implant according to the present invention includes threads having a relatively shallow flank angle and a transition area that substantially reduces the width of the thread root. In some embodiments, each thread flange includes a transition point at which the flank angle transitions from a first angle to a second angle of lesser amount than the first angle. In these ways, the threaded dental implant includes a unique cored recess and provides various improvements over traditional threaded dental implants.

20 Claims, 4 Drawing Sheets

(56) References Cited

U.S. PATENT DOCUMENTS

| | | | |
|---|---|---|---|
| 2007/0218425 A1 | 9/2007 | Gatti | |
| 2008/0254411 A1* | 10/2008 | Bondar | A61C 8/0001 |
| | | | 433/174 |
| 2008/0274440 A1* | 11/2008 | Smith | A61C 8/005 |
| | | | 433/174 |
| 2008/0286720 A1 | 11/2008 | Reed | |
| 2009/0142732 A1* | 6/2009 | Kahdemann | A61C 8/0012 |
| | | | 433/174 |
| 2010/0009316 A1 | 1/2010 | Hurson | |
| 2010/0055644 A1 | 3/2010 | Arni | |
| 2010/0316970 A1 | 12/2010 | Shih et al. | |
| 2011/0195380 A1 | 8/2011 | Giorno | |
| 2011/0200969 A1 | 8/2011 | Schroering | |
| 2011/0300510 A1 | 12/2011 | Heo | |
| 2012/0231419 A1 | 9/2012 | Park | |
| 2012/0257945 A1* | 10/2012 | Phua | F16B 25/0047 |
| | | | 411/311 |

OTHER PUBLICATIONS

Semblex Corporation-Delta PT Sep. 17, 2008.*
Semblex Delta PT Screw PDF (Sep. 16, 2008); "Semblex".*
https://www.semblex.com/files/DeltaPT-Semblex.pdf (Accessed Apr. 24, 2015).

* cited by examiner

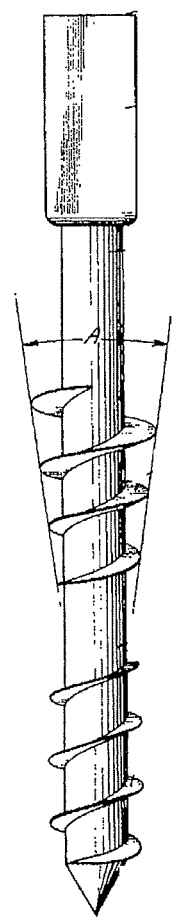
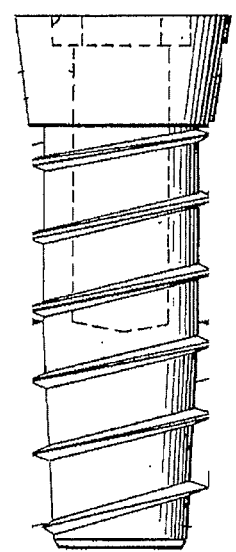
Fig. 1a
(Prior Art)
Fig. 1b
(Prior Art)

THREADED DENTAL IMPLANT

FIELD OF THE INVENTION

The present invention relates generally to the field of dentistry. More particularly, the present invention relates to threaded dental implants.

BACKGROUND

Typical threaded dental implants, such as those shown in FIG. 1a and FIG. 1b, include large flat root sections and/or steeply angled thread flanks. Either of these features alone can cause material jam. In the case of a threaded dental implant, these features can cause bone material to jam in the threads of the implant.

Material jam in bones can lead to stress concentrations and potentially bone fractures. A bone fracture can cause an otherwise successful threaded dental implant procedure to be considered a failure. As a result, current threaded dental implants have a high percentage failure rate. Furthermore, threaded dental implants having steep thread flank angles generate high side wall pressure and radial stress, generate high heat during installation, do not provide for sufficient thread surface area, and, in some cases, exhibit poor joint stability.

Consequently, it would be beneficial to have a threaded dental implant that minimized stress concentrations so as to minimize bone fractures. Furthermore, it would be beneficial to have a threaded dental implant that generated lower side wall pressure and radial stress, generated less heat during installation, provides for sufficient thread surface area, and exhibits superior joint stability.

SUMMARY

A threaded dental implant according to the present invention includes threads having a relatively shallow flank angle. In one embodiment the flank angle is between approximately 20 and 30 degrees. In another embodiment, the flank angle transitions from approximately 30 degrees to approximately 20 degrees A threaded dental implant includes a shaft having first and second ends. In one embodiment the shaft is essentially a solid cylinder having an exterior surface that defines a relatively constant first diameter. In such an embodiment, threads extend radially from the first diameter of the shaft in a helical pattern between the first and second ends of the shaft. Between the threads, the first diameter of the shaft defines a helical root of the threads.

Some embodiments of the present invention include a relatively substantial transition section between the threads and the shaft. In some embodiments, the combination of the relatively shallow flank angles of the threads and the relatively substantial transition sections between the threads and the shaft provides smaller thread roots than are provided by traditional threads. This leads to increased flank engagement, and optimized bone flow. Additionally, in some embodiments, the helix angle of the thread has also been optimized to allow for more thread engagement per length of implant.

The foregoing and other objects are intended to be illustrative of the invention and are not meant in a limiting sense. Many possible embodiments of the invention may be made and will be readily evident upon a study of the following specification and accompanying drawings comprising a part thereof. Various features and subcombinations of invention may be employed without reference to other features and subcombinations. Other objects and advantages of this invention will become apparent from the following description taken in connection with the accompanying drawings, wherein is set forth by way of illustration and example, an embodiment of this invention and various features thereof.

BRIEF DESCRIPTION OF THE DRAWINGS

A preferred embodiment of the invention, illustrative of the best mode in which the applicant has contemplated applying the principles, is set forth in the following description and is shown in the drawings and is particularly and distinctly pointed out and set forth in the appended claims.

FIG. 1a is a side view of a first traditional threaded dental implant;

FIG. 1b is a side view of a second traditional threaded dental implant;

DETAILED DESCRIPTION

As required, a detailed embodiment of the present invention is disclosed herein; however, it is to be understood that the disclosed embodiment is merely exemplary of the principles of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 2:
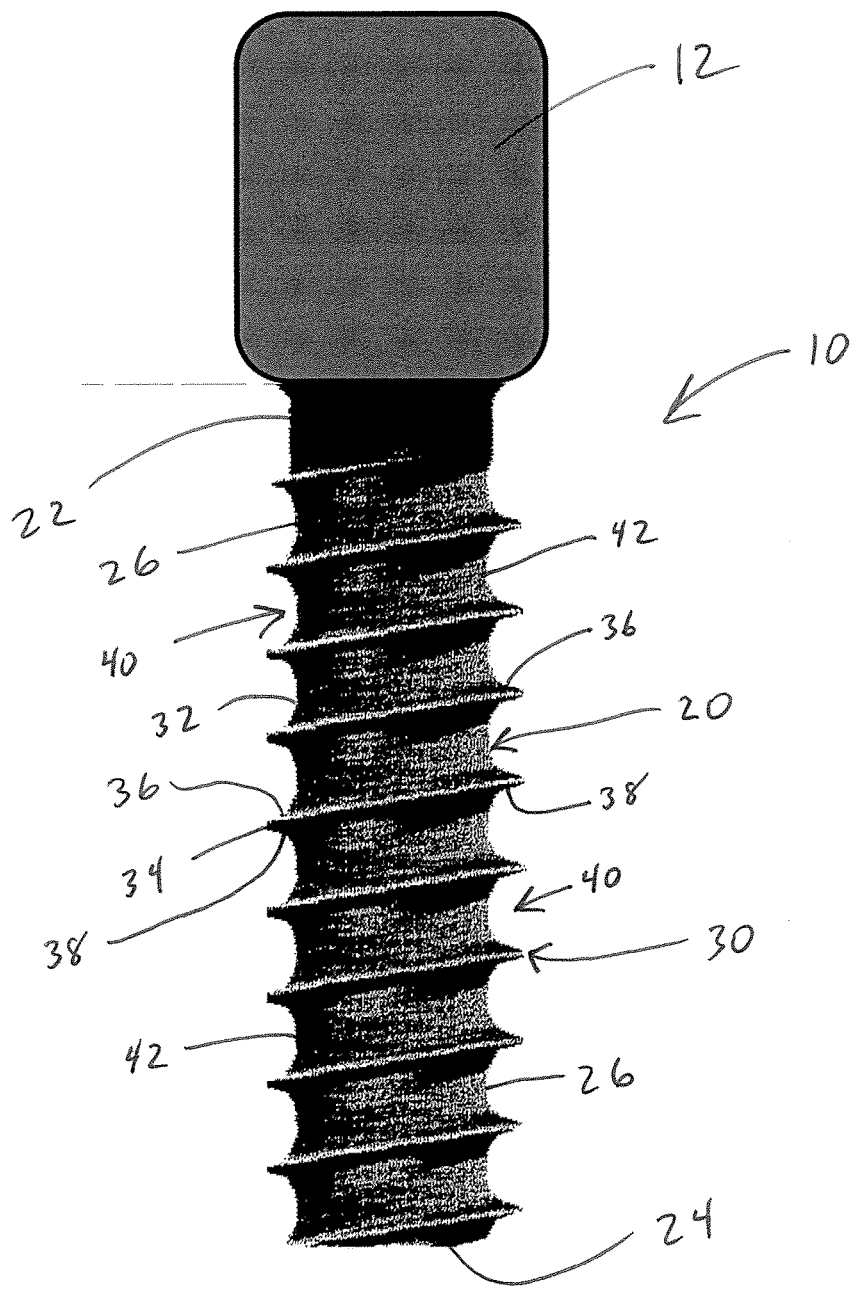
FIG. 2 is a side view of an embodiment of a threaded dental implant of the present invention.
Figure 3:
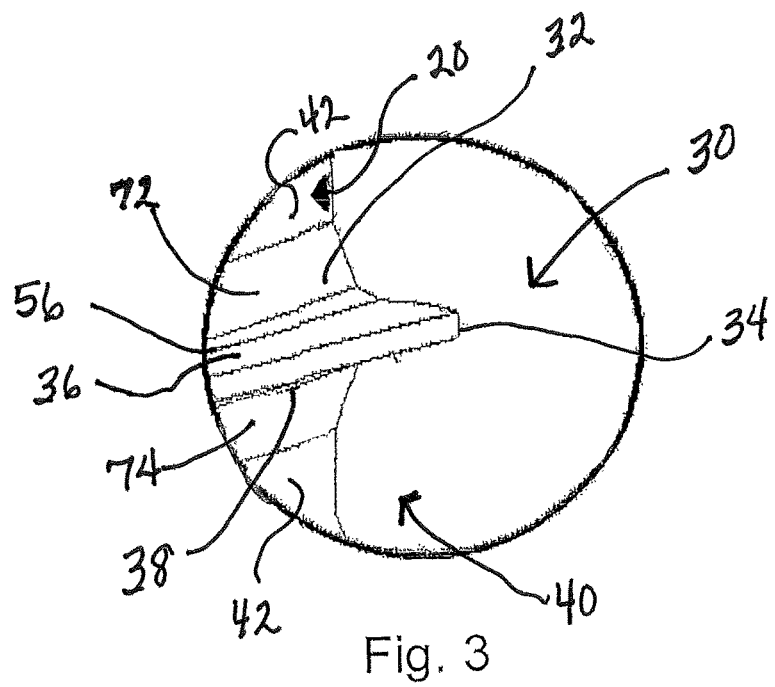
FIG. 3 is an isolated view on an enlarged scale of a portion of FIG. 2.
Figure 4:
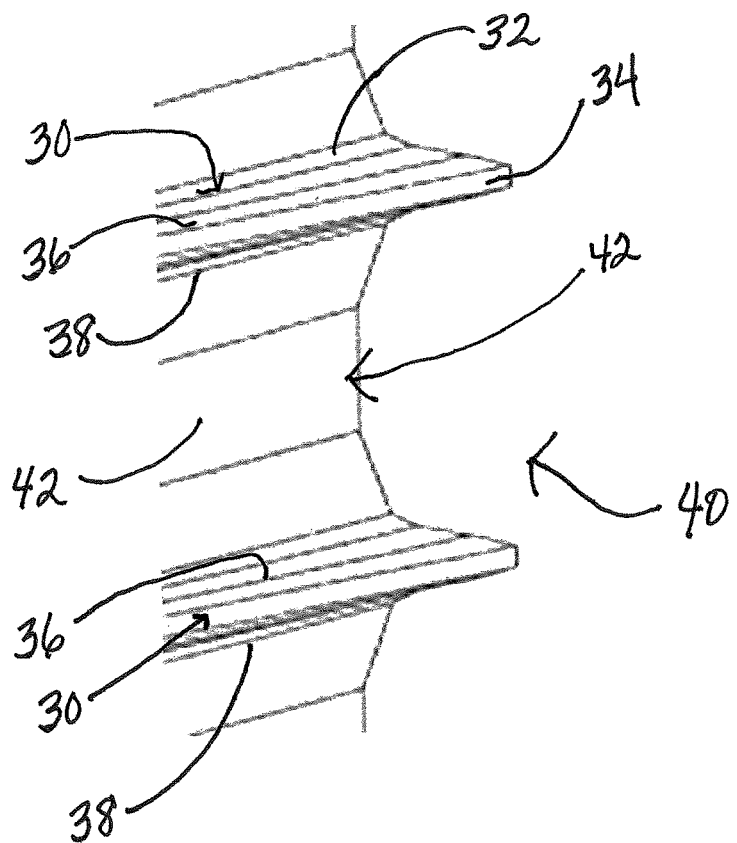
FIG. 4 is an isolated view on an enlarged scale of a portion of FIG. 2.

Referring now to the invention in more detail, a threaded dental implant 10 includes a shaft 20 having first 22 and second 24 ends. (FIG. 2). In some embodiments, the shaft 20 is a solid cylinder having an exterior surface 26 that defines a first diameter. Threads 30 extend radially from the first diameter of the shaft 20 in a helical pattern between the first 22 and second 24 ends of the shaft 20.

The threads 30 include a proximal end 32 coupled to the shaft 20 and a distal end 34 opposed to the proximal end 32 of the threads. In some embodiments, a first flank 36, and an opposed second flank 38 extend from the distal end 34 of the threads 30 towards the proximal end 32 of the threads, thereby defining a flank angle. In some embodiments, the flank angle is between approximately 20 and 30 degrees. In other embodiments, the flank angle transitions from approximately 30 degrees near the distal end 34 of the threads 30 to approximately 20 degrees nearer the proximal end 32 of the threads 30.

The distal end 34 of the threads 30 defines a major diameter of the threads 30 while the exterior surface 26 of the shaft 20 defines a minor diameter of the threads 30. A thread pitch of the threads 30 is defined as the axial distance between one major diameter of the threads 30 and the next major diameter of the threads 30.

Figure 6:
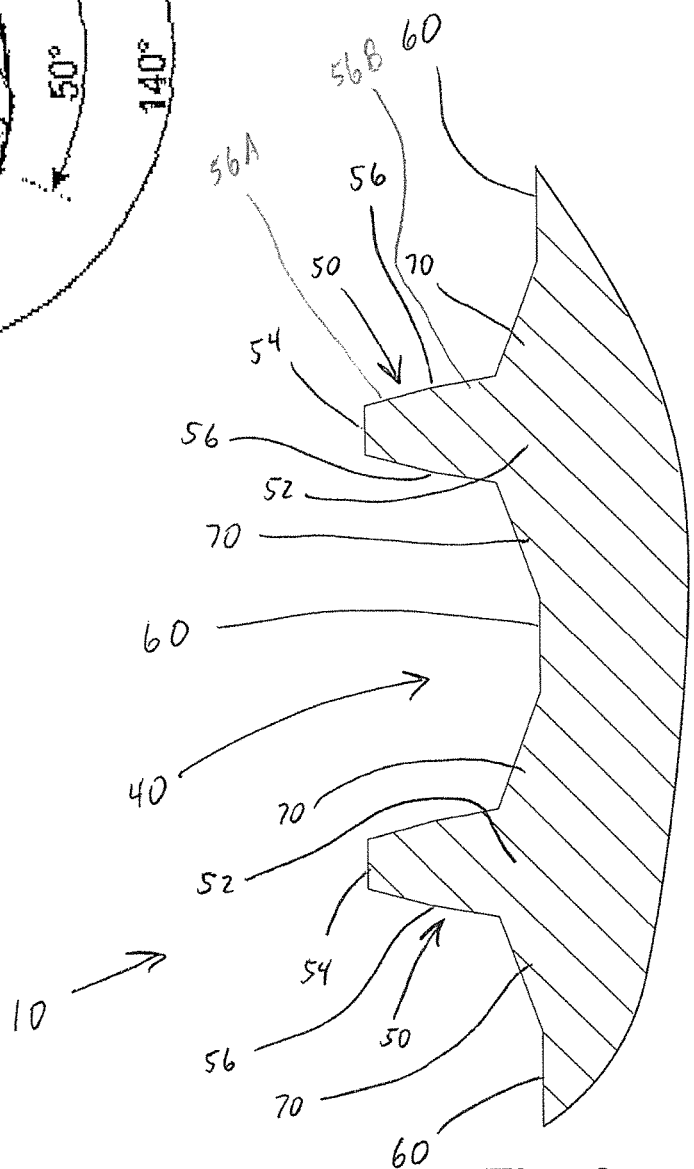
FIG. 6 is another isolated cross-sectional view of a portion of FIG. 2.

As shown in FIG. 6, a cross section of the threaded dental implant 10 displays the threads 30 as a plurality of thread flanges 50 extending radially from the shaft 20. Each thread flange 50 includes a proximal end 52 coupled to the shaft 20 and an opposed distal end 54. Due to the relatively shallow flank angles of the threads, the rate at which the thickness of each thread flange 50 increases relative to the distal end 54 of the thread flange 50 is less than the rate at which the thickness of each thread flange 50 increases on a traditional threaded dental implant having traditional flank angles.

Figure 5:
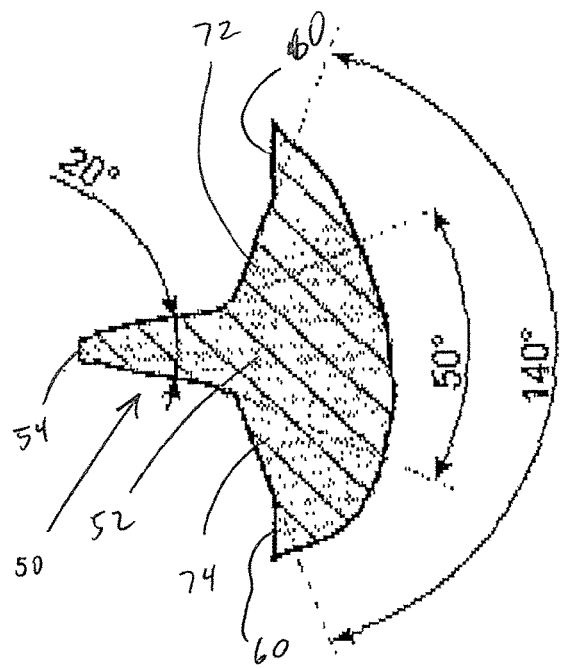
FIG. 5 is an isolated cross-sectional view of a portion of FIG. 2.

Also shown in FIG. 6, a cross section of the threaded dental implant displays the first diameter of the shaft as a plurality of flat areas 60, each flat area 60 being located between two thread flanges 50. In traditional threaded dental implants, the flat areas 60 are relatively large extending from a first thread flange to an adjacent thread flange. In at least some embodiments of the present invention, the flat areas 60 are substantially reduced by including a transition area 70 between the shaft 20 and the threads 30. In one such embodiment, a first 72 and second 74 transition area is displayed in the cross section of FIG. 5 as extending between a thread flange 50 at angles of approximately thirty degrees relative to the flat areas 60 defined by the first diameter of the shaft 20. In this way, the transition areas 70 reduce the length of the flat areas 60. Additionally, the transition areas 70 effectively increase the width of the proximal ends 52 of the thread flanges 50 by substantially increasing the flank angle (to approximately 140 degrees in the described example) near the proximal end 52 of the thread flanges 50 as opposed to the relatively shallow flank angles near the distal ends 54 of the thread flanges 50. By wrapping the defined cross-sectional features of the thread flanges 50 and transition areas 70 around the outer surface 26 of the shaft 20 in a helical pattern, the flat areas 60 define a helical thread root 42 at the base of a helical cored recess 40.

In some embodiments, each thread flange 50 defines a transition point 56 at which the flank angle transitions from a first angle 56A to a second angle 56B. In some such embodiments, the first angle is approximately 30 degrees and the second angle is approximately 20 degrees. This reduces the radial stress and eliminates bone cracking by reducing sidewall bone pressure and allows for smooth flow of bone material inward with minimal outward stresses Transition areas 70 further assist with the flowing of bone material into the root of the thread. It will be appreciated that in various embodiments, alternative values of the first angle 56A and second angle 56B will be utilized. In some such embodiments the first angle 56A is between 29 and 31 degrees, and the second angle 56B is between 19 and 21 degrees. In other embodiments, still other angle values are utilized, and the differentiation between the first angle 56A and second angle 56B will vary, so long as the angle transitions from a greater value of the first angle 56A to a lesser value of the second angle 56B.

In some embodiments a small helix angle and/or a unique cored recess 40 allows for natural flow of bone material during and after installation. In some such embodiments, the helix angle is approximately between five (5) and seven (7) degrees.

In some embodiments, each thread flange 50 defines a transition radius (not shown) rather than a transition point 56. In such embodiments, the flank of the thread includes an arc or rounded feature transitioning from a first flank angle into a second flank angle. In some such embodiments, the lack of sharp angles at the transition radius allows for even more smooth bone flow.

In other embodiments, the outline of each thread flange 50, from its distal end 54 to its proximal end 52, is completely rounded or curved such that there are no transition points at all. For instance, in some embodiments, the transition between the flanks 36, 38 and the transition areas 70, 72, 74 defines a transition radius rather than a transition point. In some such embodiments, the transition between the transition areas 70 and the flat areas 60 also defines a transition radius.

The chart below shows the preferred thread pitch to diameter.

| Major Diameter-Ø | $d_1$ | 1.8 | 2.0 | 2.2 | 2.5 | 3.0 | 3.5 | 4.0 | 4.5 | 5.0 | 6.0 | 7.0 | 8.0 | 10.0 |
|---|---|---|---|---|---|---|---|---|---|---|---|---|---|---|
| Core Diameter-Ø | $d_2$ | 1.22 | 1.36 | 1.51 | 1.72 | 2.09 | 2.45 | 2.81 | 3.17 | 3.53 | 4.26 | 4.98 | 5.70 | 7.15 |
| Thread Pitch | P | 0.71 | 0.78 | 0.85 | 0.95 | 1.12 | 1.29 | 1.46 | 1.63 | 1.80 | 2.14 | 2.48 | 2.82 | 3.50 |

The construction details of the invention as shown in FIG. 2 are that the dental implant may be made of any type of metal or of any other sufficiently rigid and strong material such as high-strength plastic, metal, and the like. In some embodiments, the flank angle is constant. In other embodiments a first flank angle immediately changes to a second flank angle at a transition point 56. In still other embodiments, a first flank angle transitions to a second flank angle at a transition radius (not shown).

In use, the threaded dental implant 10 is at least partially positioned below a gum-line of a patient such that the threads 30 are at least partially in communication with a jawbone so as to secure the threaded dental implant 10 to the jawbone. In some embodiments, the threaded dental implant 10 includes an abutment 12 coupled to the first end 22 of the shaft 20 and extending away from the jaw bone so as to enable securing another dental device, such as a crown, to the abutment 12.

The multi-angled thread profile and cored recess allow for improved bone flow to provide maximum bone to implant engagement, the arc or approximately 30 degree angle which backs off into a 20 degree angle allows unimpeded flow of bone material, the larger surface area enabling superior bone healing, less heat build up during installation and less radial stress and side wall pressure providing for superior implant stability and allows for thinner bone substrate necessary to achieve implant stability, an increased number of threads are engaged in the bone when compared to conventional implant thread higher mechanical strength and improved serviceability. The almost flat pitch allows more threads to engage in bone areas with porosity, pockets or voids. The thread allows for a high clamp load at smaller contact pressure by the increased flank engagement. The lower pressure allows for faster healing, less patient discomfort and a more stable implant.

Other various advantages of the inventive concept include, but are not necessarily limited to:

offering higher clamp load at smaller contact pressure by means of high flank engagement;

the thread design provides for reduction of fastener length and/or diameter as well as improved tensile and torsional stress;

lower drive torque and less material displacement allowing for less radial stress;

high strip to drive torque ratios;
greatly reduced bone expansion and cracking; and
greater pullout strength.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

I claim:

1. A threaded dental implant comprising:
   an abutment that is configured for securing a dental crown within a patient's mouth when the threaded dental implant is secured to a jawbone of the patient that includes areas of porosity, pockets, and/or voids;
   a shaft having a first end coupled to said abutment, an opposed second end displaced from said abutment, and an exterior surface extending between said first and second ends; and
   a thread flange having a proximal end coupled to said shaft and an opposed distal end displaced from said shaft, said thread flange being wrapped around said shaft in a helical pattern so as to create threads having a proximal end coupled to said shaft and an opposed distal end defining a major diameter of the threads;
   wherein said threads include opposed first and second flanks extending from the distal end of the threads towards the proximal end of the threads, thereby defining a flank angle;
   wherein said flank angle defines a first angle at a first location between said proximal and distal ends of said thread flange,
   wherein said flank angle further defines a second angle at a second location between said first location and said proximal end of said thread flange, and
   wherein said first angle is larger than said second angle to allow for unimpeded flow of bone material during installation.

2. The threaded dental implant of claim 1, wherein said flank angle transitions from said first angle to said second angle at a transition point.

3. The threaded dental implant of claim 2, wherein said first angle is approximately 30 degrees and said second angle is approximately 20 degrees.

4. The threaded dental implant of claim 1, wherein said flank angle transitions from said first angle to said second angle at a transition radius.

5. The threaded dental implant of claim 4, wherein said first angle is approximately 30 degrees and said second angle is approximately 20 degrees.

6. A threaded dental implant comprising:
   an abutment that is configured for securing a dental crown within a patient's mouth when the threaded dental implant is secured to a jawbone of the patient that includes areas of porosity, pockets, and/or voids;
   a shaft having a first end coupled to said abutment, an opposed second end displaced from said abutment, and an exterior surface extending between said first and second ends;
   a thread flange having a proximal end coupled to the shaft and an opposed distal end displaced from said shaft, said thread flange being wrapped around said shaft in a helical pattern so as to create threads having a proximal end coupled to said shaft and an opposed distal end defining a major diameter of the threads, wherein said threads are configured with a first pitch along a first section of said thread flange and second pitch along a second section of said thread flange; and
   a transition area between the shaft and the threads, said transition area being wrapped around said shaft in the same helical pattern as the thread flange so as to create a cored recess to allow for natural flow of bone material during installation.

7. The threaded dental implant of claim 6, wherein a base of said cored recess is defined by said exterior surface of said shaft so as to define a thread root.

8. The threaded dental implant of claim 6, wherein:
   said threads include a first flank and an opposed second flank extending from the distal end of the threads towards the proximal end of the threads, thereby defining a flank angle;
   said first and second flanks extend onto said transition area; and
   said flank angle is approximately 140 degrees at said transition area.

9. The threaded dental implant of claim 8, wherein said flank angle transitions from a first angle to a second angle prior to transitioning to the approximately 140 degrees at said transition area.

10. The threaded dental implant of claim 9, wherein said first angle is approximately 30 degrees and said second angle is approximately 20 degrees.

11. The threaded dental implant of claim 10, wherein said flank angle transitions from said first angle to said second angle at a transition point.

12. The threaded dental implant of claim 10, wherein said flank angle transitions from said first angle to said second angle at a transition radius.

13. The threaded dental implant of claim 10, wherein said flank angle transitions from said second angle to said approximately 140 degrees at said transition area at a transition radius.

14. The threaded dental implant of claim 13, wherein said flank angle transitions from said approximately 140 degrees at said transition area to an exterior surface of said shaft defining a thread root so that said cored recess does not include sharp angles.

15. The threaded dental implant of claim 14, wherein said threads define a helix angle between five and seven degrees.

16. A method of installing a dental crown, the method comprising:
   securing a dental implant to a jawbone of a dental patient that includes areas of porosity, pockets, and/or voids; and
   securing the dental crown to an abutment of the dental implant,
   wherein the dental implant comprises:
   a shaft having a first end coupled to said abutment, an opposed second end displaced from said abutment, and an exterior surface extending between said first and second ends; and
   a thread flange having a proximal end coupled to said shaft and an opposed distal end displaced from said shaft, said thread flange being wrapped around said shaft in a helical pattern so as to create threads having a proximal end coupled to said shaft and an opposed distal end defining a major diameter of the threads;

wherein said threads include opposed first and second flanks extending from the distal end of the threads towards the proximal end of the threads, thereby defining a flank angle;

wherein said flank angle defines a first angle at a first location between said proximal and distal ends of said thread flange, wherein said flank angle further defines a second angle at a second location between said first location and said proximal end of said thread flange, and wherein said first angle is larger than said second angle to allow for unimpeded flow of bone material during installation.

17. The method of claim 16, wherein said flank angle transitions from said first angle to said second angle at a transition point.

18. The method of claim 17, wherein said first angle is approximately 30 degrees and said second angle is approximately 20 degrees.

19. The method of claim 16, wherein said flank angle transitions from said first angle to said second angle at a transition radius.

20. The method of claim 19, wherein said first angle is approximately 30 degrees and said second angle is approximately 20 degrees.

* * * * *